United States Patent [19]

Mortreux et al.

[11] Patent Number: 4,593,140
[45] Date of Patent: Jun. 3, 1986

[54] PROCESS FOR DIMERIZING CONJUGATED DIENES

[75] Inventors: André Mortreux, Hem; Francis Petit, Wasquehal; Philippe Denis, Villeneuve D'Ascq; Gérard Buono; Gilbert Peiffer, both of Marseilles, all of France

[73] Assignee: Societe Chimique des Charbonnages S.A., Paris, France

[21] Appl. No.: 732,544

[22] Filed: May 10, 1985

[30] Foreign Application Priority Data

May 10, 1984 [FR] France ................... 84 07189
Mar. 13, 1985 [FR] France ................... 85 03671

[51] Int. Cl.$^4$ .............................................. C07C 2/02
[52] U.S. Cl. ................................. 585/508; 585/509
[58] Field of Search ............................ 585/508, 509

[56] References Cited

U.S. PATENT DOCUMENTS

| | | | |
|---|---|---|---|
| 3,641,175 | 2/1972 | Wilke et al. | 585/508 |
| 3,794,692 | 2/1974 | Akutaqawa et al. | 585/508 |
| 3,848,015 | 11/1974 | Wilke et al. | 585/508 |
| 4,025,570 | 5/1977 | Cramer | 585/508 |

*Primary Examiner*—Curtis R. Davis
*Attorney, Agent, or Firm*—Millen & White

[57] ABSTRACT

The process according to the invention consists in dimerizing a conjugated diene in the presence of a catalyst obtained by bringing together (A) at least one nickel complex of formula $NiZ_q$ in which q is the coordination number of the nickel and Z is at least one ligand capable of complexing nickel and (B) at least one phosphorus-containing ligand of general formula

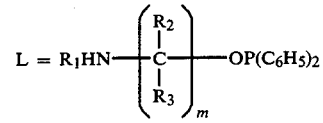

in which:
$R_1$ is chosen from a hydrogen atom and hydrocarbon radicals,
$R_2$ and $R_3$, which may be identical or different, are chosen from a hydrogen atom and hydrocarbon radicals optionally bearing at least one group chosen from alcohol, thiol, thioether, amine, imine, acid, ester, amide and ether groups, and
m is greater than or equal to 1.

14 Claims, No Drawings

PROCESS FOR DIMERIZING CONJUGATED DIENES

FIELD OF THE INVENTION

The present invention relates to a process for dimerization of conjugated dienes.

BACKGROUND OF THE INVENTION

U.S. Pat. No. 3,284,529 describes the production of linear dimers of conjugated diolefin aliphatic compounds by bringing these compounds to a temperature of 70° to 160° C. in the presence of a zerovalent nickel catalyst derived from nickel carbonyl, and in the presence of a phenolic compound as co-catalyst, the said nickel catalyst being present in the proportion of 0.5 to 5% by weight of the said diolefin compound and the said phenolic co-catalyst being present in the proportion of 10 to 35% by weight of the said diolefin compound.

SUMMARY OF THE INVENTION

An object of the present invention consists in dimerizing conjugated dienes at a rate and with a selectivity distinctly greater than those hitherto known from the processes studied previously. Another object of the present invention consists in selectively dimerizing 1,3-butadiene to 1,3,6-octatriene, 2,4,6-octatriene or 1,3,7-octatriene, in a yield distinctly greater than those hitherto known from the processes studied previously.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the abovementioned objects, and in accordance with the purpose of the invention, as embodied and broadly described herein, the invention comprises a process for dimerization of conjugated dienes in the presence of a catalyst containing zerovalent nickel and a phosphorus compound, wherein the said catalyst is obtained by bringing together (A) at least one nickel complex of formula $NiZ_q$ in which q is the coordination number of the nickel and Z is at least one ligand capable of complexing nickel and (B) at least one phosphorus-containing ligand of general formula

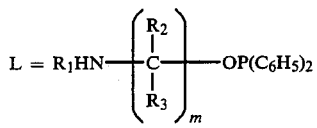

in which:

$R_1$ is chosen from a hydrogen atom and hydrocarbon radicals, $R_2$ and $R_3$, which may be identical or different, are chosen from a hydrogen atom and hydrocarbon radicals optionally bearing at least one group chosen from alcohol, thiol, thioether, amine, imine, acid, ester, amide and ether groups, and m is greater than or equal to 1.

The characteristic of the process according to the invention thus resides in the presence of a catalytic quantity of at least one ligand L, an essentially monodentate chelate of the aminophosphinite family. The ligands of this family can be identified by means of their proton, carbon-13 and phosphorus-31 nuclear magnetic resonance spectra.

The ligand L used in the process according to the invention can be obtained by reacting, in a hydrocarbon solvent at a temperature between −50° C. and 110° C. and under an inert gas atmosphere, an amino alcohol of general formula

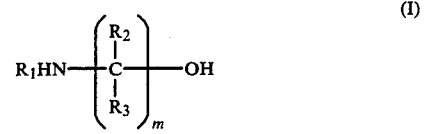

in which m, $R_1$, $R_2$ and $R_3$ have the same significance as above, with at least one compound of formula $P(C_6H_5)_2$—Y in which Y is chosen from halogen atoms and amine radicals, said compound being in a molar ratio, relative to the amino alcohol, greater than or equal to 1.

The dimerization process according to the invention can be advantageously carried out at a temperature between 0° and 120° C., under a pressure between 1 and 15 bars for a period between 2 and 400 minutes and, where appropriate, in the presence of a solvent, such as, for example, toluene.

DESCRIPTION OF THE PREFERRED EMBODIMENTS

The subject of the invention is a process for dimerization of conjugated dienes in the presence of a catalyst containing zerovalent nickel and a phosphorus compound, wherein the said catalyst is obtained by bringing together (A) at least one nickel complex of formula $NiZ_q$ in which q is the coordination number of the nickel and Z is at least one ligand capable of complexing nickel and (B) at least one phosphorus-containing ligand of general formula

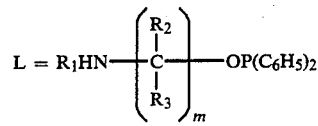

in which:

$R_1$ is chosen from a hydrogen atom and hydrocarbon radicals, $R_2$ and $R_3$, which may be identical or different, are chosen from a hydrogen atom and hydrocarbon radicals optionally bearing at least one group chosen from alcohol, thiol, thioether, amine, imine, acid, ester, amide and ether groups, and m is greater than or equal to 1.

Examples of radicals $R_2$ or $R_3$ are, in particular, methyl, isopropyl, isobutyl, isoamyl, n-hydroxyethyl, isohydroxyethyl, n-aminobutyl, 4-methyleneimidazolyl, N-n propylguanidyl, ethanoyl, acetamido, n-propionyl, n-propionamido, benzyl, p-hydroxybenzyl, 3-methyleneindoxyl, methanethioyl radicals, and the like.

The characteristics of the process according to the invention thus reside in the presence of a catalytic quantity of at least one ligand L, an essentially monodentate chelate of the aminophosphinite family. The ligands of this family can be identified by means of their proton, carbon-13 and phosphorus-31 nuclear magnetic resonance spectra.

Table I below summarises the identification data for some aminophosphinites depending on the amino alcohol or amino acid from which they originate:

TABLE I

| Aminoalcohol or Aminoacid | $\delta_P{}^{31}$ | $\delta_C{}^{13}$ | $\delta_H{}^1$ |
|---|---|---|---|
| Ephedrine | 112.3 | 127–132 (m) | 0.92–1.03 (d) (3H) |
|  |  | 84.5 (d) | 1.59 (s) (1H) |
|  |  | 61.1 (d) | 2.23 (m) (3H) |
|  |  | 31.8 (s) | 2.82 (m) (1H) |
|  |  | 15.2 (s) | 4.78–5.01 (m) (1H) |
|  |  |  | 7.27 (m) (10H) |
| Valine | 113.7 | 127–135 (m) |  |
|  |  | 69.2 (d) |  |
|  |  | 65.9 (d) |  |
|  |  | 34.5 |  |
|  |  | 29.3 |  |
|  |  | 18.9 |  |
|  |  | 18.8 |  |
| Prolinol | 113.1 |  | 1.69 (m) (5H) |
|  |  |  | 2.85 (m) (2H) |
|  |  |  | 3.20 (m) (1H) |
|  |  |  | 3.64–3.87 (m) (2H) |
|  |  |  | 7.4 (m) (10H) |
| Glycine | 113.5 |  | 1.31 (s) (1H) |
|  |  |  | 2.30 (s) (3H) |
|  |  |  | 2.73 (t) (2H) |
|  |  |  | 3.80–3.97 (t-d) (2H) |
|  |  |  | 7.14–7.48 (m) (10H) |

In this table, δ denotes the chemical shift expressed in ppm relative to phosphoric acid (in the case of phosphorus-31 NMR) or tetramethylsilane (in the case of proton and carbon-13 NMR). The symbols (m), (d), (t), (t-d), and (s) denote, respectively, a multiplet, doublet, triplet, split triplet and singlet.

The ligand L used in the process according to the invention can be obtained by reacting, in a hydrocarbon solvent at a temperature between −50° C. and 100° C. and under an inert gas atmosphere, an amino alcohol of general formula

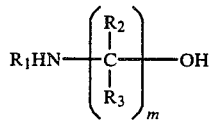

(I)

in which m, $R_1$, $R_2$ and $R_3$ have the same significance as above, with at least one compound of formula $P(C_6H_5)_2$—Y in which Y is chosen from halogen atoms and amine radicals, said compound being in a mole ratio, relative to the amino alcohol, greater than or equal to 1.

For the synthesis of the aminophosphinites, it is preferable to use compounds in which Y is an amine radical. By hydrocarbon solvent there is understood, for example, benzene, toluene and the like. To promote the removal of the hydrochloric acid formed in the reaction in the case where Y is a halogen, the reaction can be advantageously performed in the presence of an excess of tertiary amine such as, for example, triethylamine, which will precipitate in the form of hydrochloride. The phosphorus-containing ligand is successively isolated by filtering the precipitate followed by evaporation of the hydrocarbon solvent under vacuum. It generally takes the form of a viscous oil or a solid of low melting point. The amino alcohols of formula (I) are moste frequently either commercial products or they are readily accessible by reduction of amino acids (or their formylated methyl esters). When the radical $R_2$ or $R_3$ of the amino alcohol of formula (I) is the bearer of a functional group, the latter can be produced by a well-known functionalisation reaction; for example, the ester group will be introduced by esterification of the corresponding acid group (the case of carbalkoxyhydroxyprolines). By way of examples, there may be mentioned prolinol, hydroxyproline, ephedrines and N-methylated amino alcohols derived from the following natural amino acids: glycine, phenylgycine, phenylalanine, leucine, serine, threonine, histidine, lysine, arginine, isoleucine, valine, alanine, tyrosine, tryptophan, methionine, cysteine, glutamine, asparagine, aspartic acid, glutamic acid, cystine, and the like.

Among the ligands Z which are commonly usable, there may be mentioned carbon monoxide, halogens, olefins, dienes, carbonate, carboxylates and acetylacetone. The coordination number q can commonly be between 2 and 4 inclusive, depending on the ligand used.

When the ligand Z is ionic (the case of halogens, carboxylates, acetylacetone and carbonate), the dimerization reaction according to the invention can be advantageously performed in the presence of (C) at least one organometallic activator. The activator (C) can be chosen from the aluminium derivatives of formula $AlR_nX_{3-n}$, in which $1 \leq n \leq 3$, X is a halogen atom and R is an alkyl radical having from 1 to 12 carbon atoms, the metal derivatives of formula $MR_p$ in which M is chosen from lithium, magnesium and zinc, R is an alkyl or aryl radical having from 1 to 12 carbon atoms and p is the valency of the metal M, sodium borohydride $NaBH_4$ and lithium aluminium hydride. The constituents (A) and (C) are generally in a mole ratio (C)/(A) of between 0.01 and 10.

Among the conjugated dienes which can be dimerized according to the process of the invention, 1,3-butadiene, isoprene and piperylene may be cited.

The dimerization process according to the invention can be advantageously carried out at a temperature between 0° and 120° C., under a pressure between 1 and 15 bars for a period between 2 and 400 minutes and, where appropriate, in the presence of a solvent, such as, for example, toluene. The molar proportion of each component (A) and (B) of the catalyst used according to the invention is advatageously between 0.01 and 3% relative to the conjugated diene.

As regards 1,3-butadiene, when the dimerization reaction is performed in the presence of the components (A), (B), and optionally (C), it leads at high speed in a high yield of generally greater than or equal to 80%, to the selective formation of 1,3,6-octatriene or 2,4,6-octatriene, depending on the reaction time. Nevertheless, it is possible to orientate the dimerization preferentially towards the formation of methylenevinylcyclopentane or of 1,3,7-octatriene by performing the reaction in the presence of, in addition, (D) at least one aliphatic alcohol such as, for example, methanol. In this embodiment of the invention, the mole ratio (D)/(A) can be advantageously between 0.01 and 100.

For the invention to be better understood, it should be noted that, on bringing together the components (A) and (B) of the catalyst, a nickel complex of formula $NiZ_{q-r}L_r$ is formed in which Z, L and q have the same significance as above and r equals 1 or 2. A complex of this type is identifiable by means of its phosphorus-31 nuclear magnetic resonance spectrum.

The examples below are given by way of illustration and without implied limitation of the present invention.

EXAMPLE 1

Synthesis of a ligand L

In dry benzene under an atmosphere of nitrogen, 1 mole of dimethylaminodiphenylphosphine is reacted with 1 mole of ephedrine (rendered anhydrous by azeotropic distillation of the water with benzene). After the dimethylamine has been evolved, the benzene is evaporated under vaccum and 0.8 mole is recovered of 1-phenyl-1-(oxydiphenylphosphino)-2-(N-methylamino)-2-methylethane, designated NH EPHOS, of chemical purity assessed at 90%, which is identified by its proton, carbon-13 and phosphorus-31 nuclear magnetic resonance spectra, as shown in Table I above.

EXAMPLE 2

The reaction is performed under the same conditions as in Example 1, replacing ephedrine by prolinol (the latter can be readily obtained by reducing 2-pyrrolidinecarboxylic acid (proline) with $LiAlH_4$ suspended in tetrahydrofuran). 0.8 mole are recovered of an aminophosphinite designated NH PROLIPHOS of chemical purity assessed at 90%.

EXAMPLE 3

The reaction is performed under the same conditions as in Example 1, replacing ephedrine by glycinol (prepared from glycine by monoformylation of the amine group, esterification of the acid group and then reduction with $LiAlH_4$). 0.8 mole are recovered of an aminophosphinite designated NH GLYPHOS of chemical purity assessed at 90%.

EXAMPLES 4 TO 7

In a glass tube, there are introduced under nitrogen 2.5 millimoles of ligand L and 2.5 millimoles of bis-(1,5-cyclooctadiene)nickel. After the mixture is cooled, there is added a solution containing 125 millimoles of 1,3-butadiene in 10 cm³ of toluene. The reaction tube is closed and placed in a thermostatic bath at 40° C. Stirring is provided by a magnetically driven bar magnet. After a reaction time t (expressed in minutes), the contents of the tube is filtered on silica. A clear colorless solution is recovered, Table II below shows, as a function of the nature of the ligand L and time t used in each example, the value of the degree of conversion C (expressed in percent) and also the value of the selectivities (expressed in percent) for 1,3,6-octatriene (OCT-1), 4-vinylcyclohexene (VCH), 1,5-cyclooctadiene (COD) and 2,4,6-octatriene (OCT-2), disregarding the 1,5-cyclooctadiene originating from the decomposition of the catalyst.

TABLE II

| Example | L | t | C | OCT-1 | VCH | COD | OCT-2 |
|---|---|---|---|---|---|---|---|
| 4 | NH EPHOS | 10 | 90 | 95.8 | 3.2 | 1.0 | 0 |
| 5 | NH PROLIPHOS | 30 | 90 | 98.7 | 0.7 | 0.6 | 0 |
| 6 | NH GLYPHOS | 40 | 90 | 95.8 | 2.7 | 1.5 | 0 |
| 7 | NH EPHOS | 20 | 100 | 0 | 3.8 | 0.8 | 87.8 |

In example 7, the other products formed, equivalent to 7.6%, are isomers.

EXAMPLE 8 TO 11

The dimerization of 1,3-butadiene is performed under conditions similar to those of example 4, that is to say in the presence of NH EPHOS, apart from the following two exceptions:

the reaction time is changed to 60 minutes and the reaction temperature is changed to 60° C.
Methanol is also introduced in the reaction tube.

Table III below shows, as a function of the mole ratio MeOH/Ni, the selectivites (expressed in percent) for 1,3,6-octatriene (OCT-6), 1,3,7-octatriene (OCT-7), methylenevinylcyclopentane (MVCP), 4-vinylcyclohexene (VCH) and 1,5-cyclooctadiene (COD), disregarding the 1,5-cyclooctadiene originating from the decomposition of the catalyst.

TABLE III

| Example | MeOH/Ni | OCT-6 | OCT-7 | MVCP | VCH | COD |
|---|---|---|---|---|---|---|
| 8 | 0 | 88.6 | — | 3.1 | 2.6 | 5.7 |
| 9 | 2 | 38.6 | 9.4 | 13.5 | 17.7 | 20.8 |
| 10 | 12 | 27.1 | 21.9 | 39.5 | 4.2 | 6.3 |
| 11 | 36 | 3.2 | 23.9 | 60.3 | 9.4 | 3.2 |

EXAMPLES 12 AND 13

The dimerization of 1,3-butadiene is performed under conditions similar to those of Example 4, apart from the following exceptions:

the reaction temperature is changed to 60° C.,
the amounts, which are always equimolar, of ligand L and bis(1,5-cyclooctadiene)nickel introduced in the tube are decreased in accordance with Table IV below (expressed in millimoles).
the reaction time t is increased in accordance with Table IV below.

Table IV below shows the selectivities (expressed in percent) for 1,3,6-octatriene (OCT-1), 4-vinylcyclohexene (VCH) and 1,5-cyclooctadiene (COD), disregarding the 1,5-cyclooctadiene originating from the decomposition of the catalyst.

The other products formed, in the proportion of the order of 2%, are methylenevinylcyclopentane and higher oligomers.

TABLE IV

| Example | L | t | C | OCT-1 | VCH | COD |
|---|---|---|---|---|---|---|
| 12 | 0.0612 | 80 | 85 | 92.7 | 2.6 | 2.3 |
| 13 | 0.0250 | 360 | 60 | 92.8 | 2.7 | 2.5 |

EXAMPLES 14 AND 15

The dimerization of 1,3-butadiene is performed under conditions similar to those of Examples 4 and 5, that is to say in the presence of NH EPHOS or NH PROLIPHOS, apart from the following two exceptions:
the reaction time is changed to 360 minutes and the reaction temperature is changed to 60° C.
Methanol is also introduced in the reaction tube in a molar ratio of MeOH equal to 50.

Table V below shows, as a function of the nature of the ligand L, the selectivities (expressed in percent) for 1,3,6-octatriene (OCT-6), 1,3,7-octatriene (OCT-7) and methylenevinylcyclopentane (MVCP). The other products formed are higher oligomers.

TABLE V

| Example | L | OCT-6 | OCT-7 | MVCP |
|---|---|---|---|---|
| 14 | NH EPHOS | 6.3 | 27.3 | 53.3 |
| 15 | NH PROLIPHOS | 13.3 | 74.2 | 7.0 |

EXAMPLES 16 AND 17

In a glass tube, there are introduced under nitrogen 0.8 millimole of anhydrous nickel acetylacetonate and 5 cm³ of toluene. Into this solution there is introduced at 0° C., and under an atmosphere of nitrogen and butadiene, a solution containing 1.6 millimole of triethylaluminium in 5 cm³ of toluene. There are then introduced at this temperature 0.8 millimole of ligand NH EPHOS, 2 grammes of heptane and 185 millimoles of 1,3-butadiene. The reaction tube is closed and placed in a thermostatic bath stirred at 40° C. After a reaction time t (expressed in minutes), the contents of the tube are treated as in Example 4. Table VI below shows, as a function of the time t, the value of the degree of conversion C and also the selectivities for 1,3,6-octatriene (OCT-1), 4-vinylcyclohexene (VCH), 1,5-cyclooctadiene (COD) and 2,4,6-octatriene (OCT-2). The complement of the products formed to 100% consists of other unidentified dimers.

EXAMPLE 18

The dimerization of 1,3-butadiene is performed under conditions similar to those of Example 16, with the following exception: the solution of 1.6 millimole of triethylaluminium in 5 cm³ of toluene is replaced by a solution of 1.6 millimole of lithium aluminium hydride in 2 cm³ of anhydrous tetrahydrofuran. The experimental results appear in Table VI.

TABLE VI

| Example | t | C | OCT-1 | VCH | COD | OCT-2 |
|---|---|---|---|---|---|---|
| 16 | 30 | 75 | 96.4 | 1.6 | 0.9 | 0 |
| 17 | 165 | 100 | 0 | 1.8 | 1.6 | 90.2 |
| 18 | 60 | 80 | 95.0 | 1.8 | 1.3 | 0.8 |

EXAMPLE 19

In a glass tube, there are introduced under nitrogen 2,5 millimoles of the ligand prepared in example 1 and 2.5 millimoles of bis(1,5-cyclooctadiene)nickel. A solution containing 125 millimoles of 1,3-pentadiene (mixture of 28% of the cis-isomer and 72% of the trans-isomer) in 10 cm³ of toluene is added. The reaction tube is closed and placed in a thermostatic bath at 40° C., the stirring being magnetically ensured. After a reaction time of 45 minutes, the contents of the tube are filtered on silica. A clear colorless solution is recovered. The degree of conversion is equal to 75%. The analysis of the products formed shows selectivities of 70% in 4,5-dimethyloctatriene (1,3-trans, 6-trans isomer) and 21% in 4,5-dimethyloctatriene (1,3-cis, 6-trans isomer). It has not been possible to identify the other formed isomers, 9%, because each one is present in too low a concentration.

EXAMPLE 20

In a glass tube, there are introduced under nitrogen 2.9 millimoles of anhydrous nickelacetylacetonate and 5 cm³ of toluene. Into this solution is introduced a solution containing 5.8 millimoles of aluminium triethyl in 5 cm³ of toluene. Then are introduced 2.9 millimoles of the ligand prepared in example 1 and 250 millimoles of 1,3-pentadiene (mixture of 28% of the cis-isomer and 72% of trans isomer). The reaction tube is closed and placed in a stirred thermostatic bath at 40° C. After a reaction time of 240 minutes, the contents of the tube are treated in the same conditions as in example 2. The degree of conversion is equal to 85%.

The analysis of the products formed shows selectivites of 51% in 4,5-dimethyloctatriene (1,3-trans, 6-trans isomer) and 35% in 4,5-dimethyloctatriene (1,3-cis, 6-trans isomer). It has not been possible to identify the other formed isomers (14%), due to the very low content of each one.

EXAMPLE 21

Into a stainless steel autoclave reactor is introduced, under a nitrogen flow, a solution containing 2,5 millimoles of the ligand of example 1 and 2.5 millimoles of bis(1,5-cyclooctadiene)nickel in 10 cm³ of toluene. Then, 125 millimoles of isoprene are added. The reactor is closed and placed on a magnetic stirrer, the stirring being ensured by a bar magnet. A double wall placed around the autoclave permits the stabilization of the reaction temperature, by the means of a thermostatic bath set at 60° C. After a reaction time of 360 minutes, the contents of the reactor are filtered on silica. A clear colorless solution is recovered. The degree of conversion is equal to 94%. The analysis of the products formed shows the following selectivities:

| | |
|---|---|
| limonene | 5.5% |
| 2,4-dimethyl-4-vinylcyclohexene and 1,4-dimethyl-4-vinylcyclohexene | 12.5% |
| 1,4-dimethyl-1,5-cyclooctadiene and 1,5-dimethyl-1,5-cyclooctadiene | 20.5% |
| 2,7-dimethyl-1,3,6-octatriene | 3.5% |
| 2,7-dimethyl-2,4,6-octatriene | 58% |

What is claimed is:

1. Process for dimerization of a conjugated diene in the presence of a catalyst containing zerovalent nickel and a phosphorus compound, wherein the said catalyst is obtained by bringing together (A) at least one nickel complex of formula $NiZ_q$ in which q is the coordination number of the nickel and Z is at least one ligand capable of complexing nickel and (B) at least one phosphorus-containing ligand of general formula

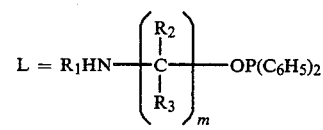

in which:

$R_1$ is chosen from a hydrogen atom and hydrocarbon radicals, $R_2$ and $R_3$, which may be identical or different, are chosen from a hydrogen atom and hydrocarbon radicals optionally bearing at least one group chosen from alcohol, thiol, thioether, amine, imine, acid, ester, amide and ether groups, and m is greater than or equal to 1.

2. Process according to claim 1, wherein Z is chosen from carbon monoxide, halogens, dienes, carbonate, carboxylates and acetylacetone.

3. Process according to claim 1, wherein q is between 2 and 4 inclusive.

4. Process according to claim 1, the ligand Z being ionic, wherein the dimerization is performed in the presence of (C) at least one organometallic activator.

5. Process according to claim 4, wherein the mole ratio (C)/(A) is between 0.01 and 10.

6. Process according to claim 1, wherein the dimerization is performed at a temperature between 0° and 120° C.

7. Process according to claim 1, wherein the dimerization is performed under a pressure of between 1 and 15 bars.

8. Process according to claim 1, wherein the dimerization is performed for a time between 2 and 400 minutes.

9. Process according to claim 1, wherein the dimerization is performed in the presence of a solvent.

10. Process according to claim 1, wherein the molar proportion of each component (A) and (B) of the catalyst is between 0.01 and 3% relative to the conjugated diene.

11. Process according to claim 1, the conjugated diene being 1,3-butadiene, wherein the dimerization is performed in the presence of (D) at least one aliphatic alcohol.

12. Process according to claim 11, wherein the mole ratio (D)/(A) is between 0.1 and 100.

13. Process according to claim 4, the conjugated diene being 1,3-butadiene, wherein the dimerization is performed in the presence of (D) at least one aliphatic alcohol.

14. Process according to claim 13, wherein the mole ratio (D)/(A) is between 0.1 and 100.

* * * * *